United States Patent
Becker et al.

(10) Patent No.: US 8,293,964 B2
(45) Date of Patent: *Oct. 23, 2012

(54) MULTILAYER LAMINATE WOUND DRESSING

(75) Inventors: Robert O. Becker, Lowville, NY (US); A. Bartholomew Flick, Lakemont, GA (US); Adam J. Becker, Scarsdale, NY (US)

(73) Assignee: Argentum Medical, LLC, Geneva, IL (US)

( * ) Notice: Subject to any disclaimer, the term of this patent is extended or adjusted under 35 U.S.C. 154(b) by 313 days.

This patent is subject to a terminal disclaimer.

(21) Appl. No.: 11/927,065

(22) Filed: Oct. 29, 2007

(65) Prior Publication Data
US 2008/0114279 A1    May 15, 2008

Related U.S. Application Data

(60) Continuation of application No. 11/220,566, filed on Sep. 6, 2005, which is a division of application No. 08/707,779, filed on Sep. 3, 1996, now Pat. No. 7,005,556, which is a continuation-in-part of application No. 08/524,134, filed on Sep. 5, 1995, now abandoned, and a continuation-in-part of application No. 08/623,046, filed on Mar. 28, 1996, now Pat. No. 5,814,094.

(51) Int. Cl.
*A61F 13/00* (2006.01)
(52) U.S. Cl. .................................................. 602/48
(58) Field of Classification Search .......... 424/445–449; 602/41–59; 604/304–308
See application file for complete search history.

(56) References Cited

U.S. PATENT DOCUMENTS

| | | | |
|---|---|---|---|
| 1,498,059 A | 6/1924 | Tyler | |
| 1,545,413 A | 7/1925 | Elmvall | |
| 1,975,518 A | 10/1934 | Rose | |
| 1,989,282 A | 1/1935 | Kimble et al. | |
| 2,577,945 A | 12/1951 | Atherton | |
| 2,934,066 A | 4/1960 | Stowasser | 128/156 |
| 2,943,627 A * | 7/1960 | Howell | 607/152 |
| 3,326,213 A | 6/1967 | Gallagher | 128/156 |
| 3,420,233 A | 1/1969 | Kanof | 128/260 |
| 3,543,760 A | 12/1970 | Bolduc | |
| 3,596,657 A | 8/1971 | Eidus | 128/156 |
| 3,799,162 A | 3/1974 | Romero-Sierra et al. | |
| 3,800,792 A | 4/1974 | McKnight et al. | 128/156 |

(Continued)

FOREIGN PATENT DOCUMENTS
DE    1161384    1/1964
(Continued)

OTHER PUBLICATIONS

Barker, et al., "The glabrous epidermis of cavies contains a powerful battery", *Am. J. Physiol.*, 242(3):R358-66 (1982).

(Continued)

*Primary Examiner* — Kim M Lewis
(74) *Attorney, Agent, or Firm* — Pabst Patent Group LLP

(57) ABSTRACT

A flexible, multilayer wound dressing with antibacterial and antifungal properties, together with methods for making the dressing. The dressing includes a layer of silver-containing fabric, a layer of absorbent material, and (optionally) a layer of flexible air-permeable and/or water-impermeable material. The dressing can be used for prophylactic and therapeutic care and treatment of skin infections and surface wounds (including surgical incisions), as a packing material, and as a swab for surface cleaning.

16 Claims, 2 Drawing Sheets

U.S. PATENT DOCUMENTS

| | | | |
|---|---|---|---|
| 3,814,097 A | 6/1974 | Ganderton et al. | |
| 3,817,253 A | 6/1974 | Gonser | |
| 3,830,908 A | 8/1974 | Klippel et al. | 424/28 |
| 3,845,771 A | 11/1974 | Vise | |
| 3,864,160 A | 2/1975 | Davidoff | |
| 3,911,906 A | 10/1975 | Reinhold, Jr. | |
| 3,914,488 A | 10/1975 | Gorrafa et al. | |
| 3,934,066 A | 1/1976 | Murch | 428/248 |
| 3,964,477 A | 6/1976 | Ellis et al. | 128/172.1 |
| 4,027,393 A | 6/1977 | Ellis et al. | 32/10 A |
| 4,034,750 A | 7/1977 | Seiderman | 128/155 |
| 4,035,500 A | 7/1977 | Dafter, Jr. | |
| 4,042,737 A | 8/1977 | Forsgren et al. | |
| 4,142,521 A | 3/1979 | Konikoff | 128/82.1 |
| 4,161,470 A | 7/1979 | Calundann | |
| 4,181,127 A | 1/1980 | Linsky et al. | |
| 4,213,463 A | 7/1980 | Osenkarski | |
| 4,240,437 A | 12/1980 | Church | |
| 4,291,125 A | 9/1981 | Greatbatch | 435/240 |
| 4,297,995 A | 11/1981 | Golub | 128/156 |
| 4,312,340 A | 1/1982 | Donadelli | |
| 4,313,438 A | 2/1982 | Greatbatch | 128/207.21 |
| 4,333,449 A | 6/1982 | Muller et al. | 128/155 |
| 4,420,529 A | 12/1983 | Westhead | |
| 4,456,001 A | 6/1984 | Pescatore | |
| 4,476,590 A | 10/1984 | Scales et al. | 3/1.91 |
| 4,486,488 A | 12/1984 | Pietsch et al. | 424/294 |
| 4,509,535 A | 4/1985 | Bryan | |
| 4,510,939 A | 4/1985 | Brenman et al. | |
| 4,528,265 A * | 7/1985 | Becker | 424/654 |
| 4,529,623 A | 7/1985 | Maggs | 427/227 |
| 4,541,426 A | 9/1985 | Webster | 128/156 |
| 4,551,139 A | 11/1985 | Plaas et al. | 604/290 |
| 4,554,923 A | 11/1985 | Batters | |
| 4,556,051 A | 12/1985 | Maurer | |
| 4,563,184 A | 1/1986 | Korol | 604/368 |
| 4,588,400 A | 5/1986 | Ring et al. | |
| 4,600,001 A | 7/1986 | Gilman | 128/156 |
| 4,606,338 A | 8/1986 | Greenway et al. | 128/156 |
| 4,615,705 A | 10/1986 | Scales et al. | 623/11 |
| 4,619,252 A | 10/1986 | Ibbott | 128/82.1 |
| 4,635,624 A | 1/1987 | Gilman | 128/156 |
| 4,646,730 A | 3/1987 | Schonfeld et al. | 728/156 |
| 4,654,323 A | 3/1987 | Beitner | 514/9 |
| 4,664,118 A | 5/1987 | Batters | |
| 4,671,266 A | 6/1987 | Lengyel et al. | 128/156 |
| 4,728,323 A | 3/1988 | Matson | 604/304 |
| 4,747,845 A | 5/1988 | Korol | 604/368 |
| 4,757,804 A | 7/1988 | Griffith et al. | 128/1.5 |
| 4,767,401 A | 8/1988 | Seiderman | 604/20 |
| 4,781,705 A | 11/1988 | Shepherd et al. | 604/289 |
| 4,798,603 A | 1/1989 | Meyer et al. | 604/378 |
| 4,817,594 A | 4/1989 | Juhasz | 128/155 |
| 4,818,697 A | 4/1989 | Liboff et al. | 435/173 |
| 4,825,877 A | 5/1989 | Kempe | 128/846 |
| 4,847,049 A | 7/1989 | Yamamoto | 422/24 |
| 4,852,453 A | 8/1989 | Morin | |
| 4,860,737 A | 8/1989 | Lang et al. | |
| 4,867,150 A | 9/1989 | Gilbert | |
| 4,867,166 A | 9/1989 | Axelgaard et al. | |
| 4,886,505 A | 12/1989 | Haynes et al. | 604/265 |
| 4,889,530 A | 12/1989 | Smith | 604/304 |
| 4,906,466 A | 3/1990 | Edwards et al. | |
| 4,909,244 A | 3/1990 | Quarfoot | 128/156 |
| 4,911,688 A | 3/1990 | Jones | 604/20 |
| 4,932,951 A | 6/1990 | Liboff et al. | 606/13 |
| 4,935,087 A | 6/1990 | Gilman | 156/251 |
| 4,937,323 A | 6/1990 | Silver et al. | |
| 4,960,413 A | 10/1990 | Sagar et al. | 604/289 |
| 4,979,946 A | 12/1990 | Gilman | 604/307 |
| 4,982,742 A | 1/1991 | Claude | 128/798 |
| 4,984,570 A | 1/1991 | Langen et al. | 128/155 |
| 4,990,144 A | 2/1991 | Blott | 604/304 |
| 4,997,425 A | 3/1991 | Shioya et al. | 604/304 |
| 5,018,515 A | 5/1991 | Gilman | 128/155 |
| 5,018,516 A | 5/1991 | Gilman | 128/155 |
| 5,019,096 A | 5/1991 | Fox, Jr. et al. | 623/1 |
| 5,038,797 A | 8/1991 | Batters | |
| 5,042,466 A | 8/1991 | McKnight | 128/155 |
| 5,049,139 A | 9/1991 | Gilchrist | 604/265 |
| 5,056,510 A | 10/1991 | Gilman | 128/155 |
| 5,067,478 A | 11/1991 | Berlant | |
| 5,130,342 A | 7/1992 | McAllister et al. | 521/61 |
| 5,133,199 A | 7/1992 | Parikh et al. | 66/192 |
| 5,147,338 A | 9/1992 | Lang et al. | 604/304 |
| 5,147,344 A | 9/1992 | Sachau et al. | 604/368 |
| 5,158,555 A | 10/1992 | Porzilli | 604/307 |
| 5,167,613 A | 12/1992 | Karami et al. | 602/42 |
| 5,180,585 A | 1/1993 | Jacobson et al. | 424/405 |
| 5,181,905 A | 1/1993 | Flam | |
| 5,185,000 A | 2/1993 | Brandt et al. | 602/63 |
| 5,266,371 A | 11/1993 | Sugii et al. | 428/40 |
| 5,275,861 A | 1/1994 | Vaughn | |
| 5,288,544 A | 2/1994 | Mallen et al. | 428/224 |
| 5,292,589 A | 3/1994 | Shepherd et al. | 428/412 |
| 5,298,015 A | 3/1994 | Komatsuzaki et al. | |
| 5,306,229 A | 4/1994 | Brandt et al. | 602/26 |
| 5,308,313 A | 5/1994 | Karami et al. | 602/55 |
| 5,320,908 A | 6/1994 | Sodervall et al. | 428/461 |
| 5,322,520 A | 6/1994 | Milder | 604/265 |
| 5,324,275 A | 6/1994 | Raad et al. | 604/265 |
| 5,326,567 A | 7/1994 | Capelli | 424/405 |
| 5,333,753 A | 8/1994 | Etheredge | 221/33 |
| 5,340,363 A | 8/1994 | Fabo | 604/304 |
| 5,360,440 A | 11/1994 | Andersen | |
| 5,374,283 A | 12/1994 | Flick | 607/46 |
| 5,395,305 A | 3/1995 | Koide et al. | |
| 5,395,398 A | 3/1995 | Rogozinski | |
| 5,405,644 A | 4/1995 | Ohsumi et al. | 427/2.31 |
| 5,413,788 A | 5/1995 | Edwards et al. | 424/409 |
| 5,419,161 A | 5/1995 | Bodenschatz et al. | 66/172 E |
| 5,429,590 A | 7/1995 | Saito et al. | 602/48 |
| 5,429,591 A | 7/1995 | Yamamoto et al. | 602/54 |
| 5,433,987 A | 7/1995 | Peterson et al. | |
| 5,454,886 A | 10/1995 | Burrell et al. | 148/565 |
| 5,465,735 A | 11/1995 | Patel | 128/888 |
| 5,470,576 A | 11/1995 | Patel | 424/445 |
| 5,470,585 A | 11/1995 | Gilchrist | 424/604 |
| 5,512,041 A | 4/1996 | Bogart | 602/58 |
| 5,520,664 A | 5/1996 | Bricault et al. | 604/265 |
| 5,543,151 A | 8/1996 | Shirai et al. | 424/448 |
| 5,569,207 A * | 10/1996 | Gisselberg et al. | 604/175 |
| 5,571,079 A | 11/1996 | Bello et al. | 602/46 |
| 5,571,521 A | 11/1996 | Lasker | 424/409 |
| 5,584,877 A | 12/1996 | Miyake et al. | |
| 5,591,790 A | 1/1997 | Lock | |
| 5,595,750 A | 1/1997 | Jacobson et al. | 424/421 |
| 5,607,683 A | 3/1997 | Capelli | 424/405 |
| 5,632,731 A | 5/1997 | Patel | 602/59 |
| 5,662,913 A | 9/1997 | Capelli | 424/405 |
| 5,681,575 A | 10/1997 | Burrell et al. | 424/423 |
| 5,695,857 A | 12/1997 | Burrell et al. | 428/209 |
| 5,714,225 A | 2/1998 | Hansen et al. | |
| 5,744,151 A | 4/1998 | Capelli | 424/405 |
| 5,753,251 A | 5/1998 | Burrell et al. | 424/426 |
| 5,770,255 A | 6/1998 | Burrell et al. | 427/2.1 |
| 5,772,620 A | 6/1998 | Szlema et al. | 602/21 |
| 5,779,659 A | 7/1998 | Allen | 602/75 |
| 5,782,785 A | 7/1998 | Herzberg | 602/26 |
| 5,782,788 A | 7/1998 | Widemire | 602/48 |
| 5,789,326 A | 8/1998 | Hansen et al. | |
| 5,814,094 A | 9/1998 | Becker et al. | 607/50 |
| 5,824,267 A | 10/1998 | Kawasumi et al. | 422/28 |
| 5,836,970 A | 11/1998 | Pandit | 606/213 |
| 5,844,013 A | 12/1998 | Kenndoff et al. | |
| 5,882,677 A | 3/1999 | Kupperblatt | |
| 5,895,419 A | 4/1999 | Tweden et al. | |
| 5,921,948 A | 7/1999 | Kawaguchi et al. | 602/52 |
| 5,974,344 A | 10/1999 | Shoemaker | 607/149 |
| 5,983,136 A | 11/1999 | Kamen | |
| 5,985,301 A | 11/1999 | Nakamura et al. | 424/404 |
| 5,985,308 A | 11/1999 | Burrell et al. | 424/426 |
| 5,998,692 A | 12/1999 | Gilding | 602/41 |
| 6,004,667 A | 12/1999 | Sakurada et al. | 428/323 |
| 6,014,585 A | 1/2000 | Stoddard | |
| 6,063,980 A | 5/2000 | Peterson et al. | |
| 6,074,965 A | 6/2000 | Bodenschatz et al. | 442/269 |

| | | | |
|---|---|---|---|
| 6,087,549 A | 7/2000 | Flick | 602/41 |
| 6,093,414 A | 7/2000 | Capelli | 424/405 |
| 6,099,489 A | 8/2000 | Herzberg et al. | 602/4 |
| 6,120,470 A | 9/2000 | Bodenschatz et al. | 602/20 |
| 6,129,694 A | 10/2000 | Bodenschatz | 602/60 |
| 6,139,856 A | 10/2000 | Kaminska et al. | 424/404 |
| 6,149,616 A | 11/2000 | Szlema et al. | 602/62 |
| 6,160,196 A | 12/2000 | Knieler et al. | 602/48 |
| 6,171,648 B1 | 1/2001 | Himmelsbach et al. | 427/208.2 |
| 6,180,544 B1 | 1/2001 | Jauchen et al. | 442/150 |
| 6,190,407 B1 | 2/2001 | Ogle et al. | 623/1.51 |
| 6,191,337 B1 | 2/2001 | Himmelsbach | 602/54 |
| 6,210,704 B1 | 4/2001 | Sasaki et al. | 424/443 |
| 6,224,898 B1 | 5/2001 | Balogh et al. | 424/445 |
| 6,224,983 B1 | 5/2001 | Sodervall et al. | 428/461 |
| 6,245,959 B1 | 6/2001 | Ohira et al. | 602/41 |
| 6,248,932 B1 | 6/2001 | Himmelsbach | 602/41 |
| 6,267,743 B1 | 7/2001 | Bodenschatz et al. | 602/62 |
| 6,267,782 B1 | 7/2001 | Ogle et al. | 623/1.1 |
| 6,274,205 B1 | 8/2001 | Himmelsbach et al. | 427/547 |
| 6,284,328 B1 | 9/2001 | Leydecker et al. | 427/496 |
| 6,322,588 B1 | 11/2001 | Ogle et al. | 623/1.46 |
| 6,333,093 B1 | 12/2001 | Burrell et al. | 428/194 |
| 6,348,212 B2 | 2/2002 | Hymes et al. | 424/449 |
| 6,350,247 B2 | 2/2002 | Bodenschatz et al. | 602/65 |
| 6,355,858 B1 | 3/2002 | Gibbins | 602/41 |
| 6,383,630 B1 | 5/2002 | Jauchen et al. | 428/383 |
| 6,428,800 B2 | 8/2002 | Greenspan et al. | 424/405 |
| 6,436,420 B1 | 8/2002 | Antelman | 424/404 |
| 6,447,470 B2 | 9/2002 | Bodenschatz et al. | 602/75 |
| 6,459,013 B1 | 10/2002 | Himmelsbach | 602/58 |
| 6,495,230 B1 | 12/2002 | do Canto | 428/41.8 |
| 6,506,957 B1 | 1/2003 | Himmelsbach et al. | 602/41 |
| 6,524,699 B1 | 2/2003 | Himmelsbach et al. | 428/343 |
| 6,551,704 B2 | 4/2003 | Himmelsbach et al. | 428/343 |
| 6,555,730 B1 | 4/2003 | Albrod et al. | 602/58 |
| 6,569,111 B2 | 5/2003 | Herzberg | |
| 6,579,539 B2 | 6/2003 | Lawson et al. | 424/618 |
| 6,582,713 B2 | 6/2003 | Newll et al. | 424/407 |
| 6,592,888 B1 | 7/2003 | Jensen et al. | 424/443 |
| 6,599,525 B2 | 7/2003 | Scamilla Aledo et al. | 424/445 |
| 6,605,751 B1 | 8/2003 | Gibbins et al. | 602/41 |
| 6,617,485 B2 | 9/2003 | Herzberg | 602/41 |
| 6,656,491 B1 | 12/2003 | Brosck et al. | 424/428 |
| 6,659,111 B1 | 12/2003 | Mouri et al. | 134/22.1 |
| 6,695,824 B2 | 2/2004 | Howard et al. | 604/305 |
| 6,706,279 B1 | 3/2004 | Hazzi | 424/443 |
| 6,713,659 B2 | 3/2004 | Bodenschatz et al. | 602/56 |
| 6,716,895 B1 | 4/2004 | Terry | 523/122 |
| 6,730,053 B1 | 5/2004 | Bodenschatz et al. | 602/64 |
| 6,822,132 B2 | 11/2004 | Ahrens et al. | 602/41 |
| 6,852,366 B2 | 2/2005 | Zschaeck | 427/356 |
| 6,861,570 B1 | 3/2005 | Flick | |
| 6,897,349 B2 | 5/2005 | Gibbins et al. | 602/48 |
| 7,005,556 B1 | 2/2006 | Becker et al. | |
| 7,230,153 B2 | 6/2007 | Flick | |
| 2001/0055608 A1 | 12/2001 | Hymes et al. | |
| 2002/0132545 A1 | 9/2002 | Lenz | 442/382 |
| 2002/0150720 A1 | 10/2002 | Howard et al. | |
| 2002/0156411 A1 | 10/2002 | Ahrens et al. | |
| 2002/0172709 A1 | 11/2002 | Nielsen et al. | 424/445 |
| 2002/0197257 A1 | 12/2002 | Meyer-Ingold et al. | 424/146.1 |
| 2003/0104039 A1 | 6/2003 | Berthold et al. | |
| 2003/0170314 A1 | 9/2003 | Burrell et al. | 424/618 |
| 2003/0176827 A1 | 9/2003 | Chandra et al. | 602/48 |
| 2003/0185901 A1 | 10/2003 | Burrell et al. | 424/618 |
| 2003/0194444 A1 | 10/2003 | Burrell et al. | 424/618 |
| 2003/0203015 A1 | 10/2003 | Aledo et al. | 424/445 |
| 2003/0208150 A1 | 11/2003 | Bruder et al. | |
| 2004/0002675 A1 | 1/2004 | Nierle et al. | 602/41 |
| 2004/0009202 A1 | 1/2004 | Woller | 424/401 |
| 2004/0010215 A1 | 1/2004 | Gibbins et al. | |
| 2004/0030276 A1 | 2/2004 | Flick | |
| 2004/0049145 A1 | 3/2004 | Flick | |
| 2004/0058013 A1 | 3/2004 | Taylor et al. | 424/618 |
| 2004/0086549 A1 | 5/2004 | Nielsen | 424/445 |
| 2004/0091521 A1 | 5/2004 | Radloff et al. | 424/449 |
| 2005/0187580 A1 | 8/2005 | Skiba | |
| 2005/0244484 A1 | 11/2005 | Flick | |
| 2007/0179522 A1 | 8/2007 | Becker et al. | |
| 2008/0033506 A1 | 2/2008 | Flick | |
| 2008/0064997 A1 | 3/2008 | Flick | |
| 2008/0119773 A1 | 5/2008 | Flick | |
| 2008/0125687 A1 | 5/2008 | Flick et al. | |

FOREIGN PATENT DOCUMENTS

| | | |
|---|---|---|
| EP | 0 099 758 | 2/1984 |
| EP | 0128338 | 12/1984 |
| EP | 0254413 | 1/1988 |
| EP | 0291587 | 11/1988 |
| EP | 0 344 090 | 11/1989 |
| EP | 0344090 | 11/1989 |
| EP | 0354315 | 2/1990 |
| EP | 0 367 320 | 5/1990 |
| EP | 0392640 | 10/1990 |
| EP | 1 159 972 | 5/2001 |
| GB | 363255 | 6/1930 |
| GB | 863875 | 3/1961 |
| GB | 2 092 006 | 8/1982 |
| GB | 2127389 | 4/1984 |
| GB | 2 134 791 | 8/1984 |
| GB | 2188135 | 9/1987 |
| JP | S56-166041 U | 12/1981 |
| JP | 58-209356 | 12/1983 |
| JP | 62-275456 | 11/1987 |
| JP | 3-146057 | 6/1991 |
| JP | 3-253575 | 11/1991 |
| WO | WO 90/08470 | 8/1990 |
| WO | WO 91/11206 | 8/1991 |
| WO | WO 92/13491 | 8/1992 |
| WO | WO 93/23092 | 11/1993 |
| WO | WO 96/13282 | 5/1996 |
| WO | WO 98/06509 | 2/1998 |
| WO | WO 99/15101 | 4/1999 |
| WO | WO 00/25726 | 5/2000 |
| WO | WO 00/73552 | 12/2000 |
| WO | WO 01/60599 | 8/2001 |
| WO | WO 02/099181 | 12/2002 |
| WO | WO 03/022317 | 3/2003 |
| WO | WO 2004/002384 | 1/2004 |
| WO | WO 2004/018020 | 3/2004 |
| WO | WO 2004/037186 | 5/2004 |
| WO | WO 2007/046806 | 4/2007 |

OTHER PUBLICATIONS

Borgens, "What is the role of naturally produced electric current in vertebrate regeneration and healing", *Int. Rev. Cytol.*, 76:245-98 (1982).

Eaglstein, "Current wound management: a symposium", *Clin. Dermatol.*, 2(3) 134-42 (1984).

Eckersley and Dudley, "Wounds and wound healing", *Br. Med. Bull.*, 44(2):423-36 (1988).

Winter, et al., Movement of epidermal cells over the wound surface In: Montagna W. & Billingham R.E Advances in Biology of the skin. vol. 5. pp. 113-127. Wound Healing. New York. The MacMillan Company (1964).

Complaint—*Argentum Medical, LLC* v. *Noble Biomaterials and Derma Sciences, Inc.*, Civil Action Case No. 1:07-cv-06769 filed Dec. 3, 2007.

U.S. Appl. No. 09/613,961, filed Jul. 11, 2000, Flick.

U.S. Appl. No. 11/255,492, filed Oct. 21, 2005, Flick et al.

Becker et al., "Clinical Exp. with Low Intensity Direct Current Stimulation of Bone Growth," *Clin. Orthop. & Rel. Res.*, (1977) vol. 124, pp. 75-83.

Becker et al., "Electrochemical Mechanisms and the Control of Biological Growth Processes," *Modern Aspects of Electrochemistry*, (1971) No. 10, pp. 289-338.

Becker et al., "Experience with Low-Current Silver Electrode Treatment of Nonunion," *Electrical Prop. Bone & Cartilage* (ed. C.T. Brighton, et al.), (1979).

Berger et al., "Electrically Generated Silver Ions: Quantitative Effects on Bacterial & Mammalian Cells," *Antimicrob. Agents & Chemother*, (1976), vol. 9, 357-358.

Complaint—*Noble Fiber Technologies, LLC* v. *Argentum Medical, LLC*, Civil Action No. 3:05-CV-01855-ARC, filed Sep. 13, 2005.

Hill et al., "Inhibitory and Cidal Antimicrobial Actions of Electrically Generated Silver Ions," *J. Oral & Maxillofac. Surg.*, (1987) vol. 45, pp. 779-784.

Marino et al., "Electrochemical Properties of Silver-Nylon Fabrics," *Electrochemical Science and Technology*, (1985) vol. 132, No. 1, pp. 68-72.

Spadaro et al., "Experience with Anodic Silver in the Treatment of Osteomyelitis," 25th Ann. ORS Mtg., (Feb. 20-22, 1979).

Spadaro et al., "Some Specific Cellular Effects of Electrically Injected Silver & Gold Ions," *Bioelectrochem. & Bioenergetics*, (1976) vol. 3, pp. 49-57.

Urist et al., "Bone Morphogenesis in Implants of Insoluble Bone Gelatin," *Proc. Nat. Acad. Sci. USA*, (1973) vol. 70, No. 12, Part I, pp. 3511-3515.

Patricia C. MacKeen, et al., *Silver-Coated Nylon Fiber as an Antibacterial Agent*, Antimicrobial Agents and Chemotherapy, p. 93-99 (American Society for Microbiology—Jan. 1987).

Edwin A. Deitch, et al., *Silver-Nylon: A New Antimicrobial Agent*, Antimicrobial Agents and Chemotherapy, pp. 356-359 (American Society for Microbiology—Mar. 1983).

Perry J. Riggle, et al., *Role of a Candida albicans P1-Type ATPase in Resistance to Copper and Silver Ion Toxicity*, Journal of Bacteriology, pp. 4899-4905 (American Society for Microbiology—Sep. 2000).

Amended Complaint—*Noble Fiber Technologies, LLC v. Argentum Medical, LLC et al.*, Civil Action Case No. 3:05-cv-01855-ARC filed Oct. 21, 2005.

Deitch, E.A. et al., *Silver-Impregnated Nylon Cloth Dressing*, Burns, Issue 5, p. 423 (Oct. 1987).

Marino, Andrew A. et al., *Electric Silver Antisepsis*, Biomedical Engineering, pp. 336-337 (IEEE Transactions on Biomedical Engineering—May 1985).

Marino, Andrew A. et al., *Electrical Augmentation of the Antimicrobial Activity of Silver-Nylon Fabrics*, Journal of Biological Physics, pp. 93-98 (1984).

McManus, A.T., *The Burn Wound: Effect of Silver Nylon Dressing and DC*, Pathophysiology, p. 121 (US Army Institute of Surgical Research—Nov. 1994).

Schierholz, J.M. et al., *Efficacy of Silver-Coated Medical Devices*, Journal of Hospital Infection, pp. 257-262 (The Hospital Infection Society—1998).

Becker R.O. and Spadaro J.A., *Treatment of Orthopedic Infections with Electrically Generated Silver Ions*, Journ. of Bone and Joint Surgery, Oct. 1978, vol. 60-A, No. 7, pp. 871-881.

Berger T.J., Spadaro J.A., Bierman, R., Chapin S.E., Becker R.O., *Antifungal Properties of Electrically Generated Metallic Ions.*, Atimicrobial-Agents and Chemotherapy, Nov. 1976, vol. 10, No. 5, pp. 856-860.

Foulds, I.S. and Barker A.T. *Human skin battery potentials and their possible role in wound healing*, British J. of Dermatology, Mar. 1983, 109 pp. 515-522.

Friedenberg Z.B. *Bioelectric Potentials in Bone*. Journ. of Bone and Joint Surgery, Jul. 1966, vol. 48-A, No. 5, pp. 915-923.

Illingworth, C.M. and Barker A.T. *Measurement of Electrical Currents Emerging During the Regeneration of Amputated Finger Tips in Children*, Clin. Phys. Physiological Measurements, 1980, vol. 1, No. 1, pp. 87-89.

Jaffe, L.F. and Vanable J.W., Jr. *Electric Fields and Wound Healing*, Clinics in Dermatology, Jul.-Sep. 1984, vol. 2, No. 3, pp. 34-44.

McCaffery M., Pasero C., Pain: *Clinical Manual*, Second Edition, Mosby, pp. 62-65 (1999).

Ohnhaus E.E. and Adler R. *Methodological Problems in the Measurement of Pain: A Comparison Between the Verbal Rating Scale and the Visual Analogue Scale*, Pain, 1975, Elsevier/North-Holland, Amsterdam, pp. 379-384.

Pain Assessment and Management: An Organizational Approach, Joint Commission, Chapter Three: Assessment of Persons with Pain, pp. 13-25 (2000).

Smee L., *The Effectiveness of Silver Nylon Cloth and Silver Sulfadiazine Cream as Antiseptics*, Piedmont College Senior Thesis, Apr. 1996, USA.

Sriwatanakul K., Kelvie W., Lasagna L., Calimlim, J.F., Weis O.F., Mehta G. *Studies with Different Types of Visual Analog Scales for Measurement of Pain*, Dept. of Pharmacol. Ther., Aug. 1983, pp. 234-239.

Spadaro J.A., Berger T.J., Barranco S.D., Chapin S.E., Becker R.O. *Antibacterial Effects of Silver Electrodes with Weak Direct Current*, Atimicrobial-Agents and Chemotherapy., Nov. 1974, vol. 6, No. 5, pp. 637-642.

Vanable J.W., Jr. *Integumentary Potentials and Wound Healing*, Elec. Fields In Vertebrate Repair, 1989, pp. 171-224.

Westaim Biomedical Commercial Literature, bearing 1988 Copyright notice and product label bearing Acticoat. RTM.

Khanna, A., Sivaraman, R., and Vohora S.B. *Analgesic Activity of Silver Preparations Used in Indian Systems of Medicine*. Indian Journal of Pharmacology, 1997, 29:393-398.

European Search Report.

Deitch, et al. "Silver nylon cloth: In vitro and in vivo evaluation of antimicrobial activity", *J. Trauma*, 27(3): 301-304 (1987).

"Magnetic field", Online Encyclopedia Article, http://en.wikipedia.org/wiki/Magnetic_field; last modified (accessed May 27, 2009).

"Ripstop nylon", Online Encyclopedia Article, http://en.wikipedia.org/wiki/Ripstop_nylon; last modified May 20, 2009; (accessed May 27, 2009).

Detailed Request for *Ex Parte* Reexamination of U.S. Patent No. 7,230,153 to Flick. The Request for Reexam was filed on Feb. 16, 2010.

Wikipedia, "Magnetic Field," URL: http://en.wikipedia.org/wiki/Magnetic_field, accessed Jun. 28, 2010.

Detailed order granting request for *ex parte* reexamination of U.S. Patent No, 7,230,153 to Flick. The order was mailed Apr. 1, 2010.

Chu, et al., "Therapeutic effects of silver nylon dressings with weak direct current on *Pseudomonas aeruginosa*-infected burn wounds," *J. Trauma*, 28(10): 1488-1492 (1988).

Chu, et al., "Multiple graft harvestings from deep partial-thickness scald wounds healed under the influence of weak direct current," *J. Trauma*, 30(8): 1044-1050 (1990).

Chu, et al., "Weak direct current accelerates split-thickness graft healing on tangentially excised second degree burns," *J. Burn Care Rehabil.*, 12: 285-93 (1991).

Chu, et al., "Enhanced survival of autoepidermal-allodermal composite grafts in allosensitized animals by use of silver-nylon dressings and direct current," *J. Trauma*, 39(2): 273-278 (1995).

Chu, et al., "Direct current reduces wound edema after full-thickness burn injury in rats," *J. Trauma*, 40(5): 738-742 (1996).

Online encyclopedia article "Resistivity," URL: http://en.wikipedia.org/wiki/Resistivity (accessed May 24, 2010).

Burrell, et al, "Efficacy of Silver-Coated Dressings as Bacterial Barriers in a Rodent Burn Sepsis Model", *Wounds*, 11(4): 64-71 (1999).

Butts, et al, *Silver: Economics, Metallurgy, and Use*, Table of Contents and Chapter 17, pp. 227-234, Van Norstrand Company, Inc., Princeton, New Jersey (1967).

Chu, et al, "Newly Made Antibacterial Braided Nylon Sutures—I. In Vitro Qualitative and in Vivo Preliminary Biocompatibility Study", *J. of Biomedical Materials Research*, 21: 1281-1300 (1987).

Thurman, et al, "The Molecular Mechanisms of Copper and Silver Ion Disinfection of Bacteria and Viruses", *CRC Critical Reviews in Environmental Controls*, 18(4) (1989).

Tredget, et al, "A matched-Pair, Randomized Study Evaluating the Efficacy and Safety of Anticoat Silver-Coated Dressing for the Treatment of Burn Wounds", *J. Burn Care Rehab*, 19: 531-537 (1998).

Tsai, et al, "In Vitro Quantitative Study of Newly Made Antibacterial Braided Nylon Structures", *Surgery, Gynecology, & Obstetrics*, 165: 207-211 (1987).

Wright, et al, "Wound Management in an Era of Increasing Bacterial Antibiotic Resistance: A Role for Topical Silver Treatment", *AJIC Am J Infect Control*, 26: 572-777 (1998).

Wright, et al., "Efficacy of Topical Silver Against Fungal Burn Wound Pathogens", *AJIC AM J Infection Control*, 27: 344-350 (1999).

Yin, et al, "Comparative Evaluation of the Antimicrobial Activity of ACTICOAT Antimicrobial Barrier Dressing", *J. Burn Care Rehab*, 20: 195-200 (1999).

Andron, et al., "Silver nylon (SN) dressings reduce leakage of Evans blue dye-albumin (EBA) into burn wounds", Abstract #1398; p. A242; Presented at Experimental Biology 1993 (Federation of American Societies of for Experimental Biology (FASEB)), New Orleans, LA, Mar. 28-Apr. 1, 1993.

Chu, et al. "Reduction of dermal ischemia (zone of stasis) by post scald application of weak direct current (DC)", *Proceedings of the American Burn Association*, vol. 25, Abstract #65, 1 page (1993). Presented at the 25th Annual Meeting of the American Burn Association, Cincinnati, OH, Mar. 24-27, 1993.

Chu, et al. "Silver-nylon (SN) and direct current (DC) reduce wound accumulation of Evans blue (EB) following full thickness thermal injury", *Wound Repair and Regeneration*, 3(1): abstract #90, 1 page, (1995). Presented at the 5th Annual Scientific Meeting of the Wound Healing Society, Minneapolis, MN, Apr. 27-30, 1995.

Chu, et al., "Accelerating split thickness graft healing on tangentially excised deep second degree burn wounds by weak direct current application", *Proceedings of the American Burn Association*, vol. 21, Abstract #62, 1 page, (1989). Twenty-First Annual Meeting, New Orleans, LA, Mar. 29-Apr. 1, 1989.

Chu, et al., "Direct current improves healing of composite auto-epidermal/allodermal grafts", *Proceedings of the American Burn Association*, vol. 26, Abstract #125, 1 page (1994). Presented at the 26th annual meeting of the American Burn Association, Orlando, FL, Apr. 20-23, 1994.

Chu, et al., "Effect of delay of direct current application on healing of partial thickness burns in Guinea pigs", *Wound Repair and Regeneration*, 4(1): abstract A147, 2 pages, (1996). Presented at 2nd Joint Meeting of the Wound Healing Society and the European Tissue Repair Society, Boston, MA, May 15-19, 1996.

Chu, et al., "Healing of second mesh auto-epidermal/allodermal composite graft without immunosuppressive treatment", Proceedings of the American Burn Association, abstract 4, p. 44, (1996). Presented at the 28th Annual Meeting of the American Burn Association, Nashville, TN, Mar. 14-17, 1996.

Chu, et al., "Improved healing and expansion with animal growth of deep partial thickness scalds treated with weak direct current silver-nylon dressings", *Proceedings of the American Burn Association*. vol. 23, abstract #172, (1991). Presented at the 23rd Annual Meeting of the American Burn Association, Baltimore, MD, Apr. 3-6, 1991.

Chu, et al., "Iontophoretic treatment of *P. mirabilis* burn wound sepsis using silver nylon dressings", *Abstracts of the 90th Annual Meeting of the American Society for Microbiology*, abstract A138, 1 page, (1990). Presented at the 1990 ASM Annual Meeting, Anaheim, CA, May 13-17, 1990.

Chu, et al., "Multiple graft harvesting from donor wounds healed under the influence of weak direct current", *Proceedings of the American Burn Association*, vol. 21, abstract #162, 1 page, (1989). Twenty-First Annual Meeting, New Orleans, LA, Mar. 29-Apr. 1, 1989.

Chu, et al., "Optimized mesh expansion of composite skin grafts in rats treated with direct current", *J. Trauma* 43(5):804-811 (1997).

Chu, et al., "Reduced contraction and hair loss after healing of guinea pig scalds treated with direct current", *Wound Repair and Regeneration*, 2(1): abstract, 1 page, (1994). Presented at the 4th Annual Wound Healing Society Meeting, San Francisco, CA, May 18-20, 1994.

Chu, et al., "Salvage of experimental full thickness scalds with cooling and weak anodal direct current", *Proceedings of the American Burn Association*, vol. 19, abstract #175, 1 page (1987). Nineteenth Annual Meeting, Washington, DC, Apr. 29-May 2, 1987.

Chu, et al., "Therapeutic effects of silver-nylon dressings with weak direct current on *Psuedomonas auerginosa* infected burn wounds", Abstract #64, vol. 17, 1 page, *American Burn Association, Seventeenth Annual Meeting*, Mar. 27-30, 1985.

Declaration of Andrew A. Marino, executed Jan. 24, 2011.

Detailed Request for *Ex Parte* Reexamination of U.S. Patent No. 7,230,153, filed Jan. 24, 2011, including Exhibits 2, 3, 6, and 18-21, letter from Scott E. Kambolz, and the Request for *Ex Parte* Reexamination Transmittal Form from Choice Therapeutics, Inc., dated Jan. 24, 2011.

LexisNexis Case Summary—*Aregentum Medical, LLC*, Plaintiff, v. *Noble Biomaterials*, and *Derma Sciences, Inc.*, Defendants. *Noble Biomaterials*, Counter-Claim Plaintiff, v. *Aregentum Medical, LLC*, Thomas Miller and Gregg Silver, Counter-Claim Defendants.—No. 3:08-CV-1305, 2010 U.S. Dist. Lexis 66037, 7 pages, (accessed Jul. 23, 2010).

Matylevich, et al., "Differential effect of direct current on extravasation of macromolecules following burn injury in rats", *Proceedings of the American Burn Association Twenty-Ninth Annual Meeting*, Abstract #33, p. S86 (1997). Twenty-ninth Annual Meeting of the American Burn Association, New York, NY, Mar. 19-22, 1997.

Matylevich, et al., "Direct current (DC) reduces albumin extravasation after partial thickness burn injury in rats", *Wound Repair and Regeneration*, 3(1): abstract 126, p. 97, (1995). Presented at the 5th Annual Scientific Meeting of the Wound Healing Society, Minneapolis, MN, Apr. 27-30, 1995.

Matylevich, et al., "Direct current (DC) reduces leakage and accumulation of macromolecules in full thickness burn injuries", *Proceedings of the American Burn Association*, vol. 26, abstract #144, 1 page (1994). Presented at the 26th annual meeting of the American Burn Association, Orlando, FL, Apr. 23, 1994.

Matylevich, et al., "Direct current (DC) reduces plasma extravasation after partial thickness burn injury in rats", *Proceedings of the American Burn Association*, abstract 170, 1 page (1995). Presented at the 27th Annual Meeting of the American Burn Association, Albuquerque, NM, Apr. 19-22, 1995.

Matylevich, et al., "Direct current reduces plasma protein extravasation after partial-thickness burn injury in rats", *J. Trauma*, 41(3):424-429 (1996).

Matylevich, et al., "Direct electric current inhibits apoptotic activity in partial thickness burn wounds in rats", *Wound Generation and Repair*, abstract 164, 2 pages (1996). Presented at 1996 2nd Joint Meeting of the Wound Healing Society and The European Tissue Repair Society, Boston, MA, May 17, 1996.

McManus & Chu, "Effective topical chemotherapy with silver-nylon (SN) dressings after excision of pseudomonas infected burn wounds", *Proceedings of the American Burn Association*, abstract #98, 1 page (1993). Presented at the 25th Annual Meeting of the American Burn Association, Cincinnati, OH, Mar. 24-27, 1993.

McManus, et al. "Mechanisms of *in vitro* sensitivity to sulfadiazine silver", *Arch. Surg.*, 118(2):161-166 (1983).

McManus, et al., "Assessment of *in vitro* minimal inhibitory concentrations of silver and ceriam ions on selected Gram-negative burn ward isolates", *Proceedings of the Tenth Annual Meeting of the American Burn Association*, abstract #10, p. 50, (1978). Birmingham, AL, Mar. 30-Apr. 1, 1978.

McManus, et al., "Studies on the mechanisms of *in vitro* resistance to silver sulfadiazine", *Proceedings of the Twelfth Annual Meeting of the American Burn Association*, abstract #34, p. 68 (1980). San Antonio, TX, Mar. 27-29, 1980.

McManus, et al., "Studies on the mechanisms of *in vitro* resistance to silver sulfadiazine", *Abstraction of the Annual Meeting of the American Society of Microbiology*, abstract A35, 1 page (1979). 79th Annual Meeting, Los Angeles, CA, May 4-8, 1979.

Order Granting a second Request for *Ex Parte* Reexamination of U.S. Patent No. 7,230,153, U.S. Appl. No. 90/011,455 to Flick. The order was mailed Mar. 7, 2011.

Becker, "Expert Opinion", date-stamped Nov. 13, 1986.

Bertuleit, "Elektrische leitfähigkeit auf polyamiden durch versilberung", *International Textile Reports*, Dec. 1990.

Bertuleit, "Elektrische leitfähigkeit auf polyamiden durch versilberung", *Techtex Forum*, Nov. 1990: 20-22 (1990).

Bertuleit, "Neue möglichkeiten für smart textiles mit leitfähigen silberfäden", http://www.statex.biz/ger/index.php?varx=smart, pp. 1-4 (accessed Jan. 22, 2009).

Bertuleit, "Silver coated polyamide: a conductive fabric", *J. Coated Fabrics*, (20): 211-215 (1991).

Chu, et al. "Multiple graft harvestings from deep partial-thickness scald wounds healed under the influence of weak direct current", *J. Trauma*, 30(8):1044-9; discussion 1049-50 (1990).

Chu, et al. "The use of transplantable dermis from incompatible host in composite skin grafts: paper 54", *Proceedings ABA 33rd Annual Meeting* (Boston, MA); p. S73 (2001).

Chu, et al. "Therapeutic effects of silver nylon dressings with weak direct current on *Pseudomonas aeruginosa*-infected burn wounds", *J. Trauma*, 28(10):1488-92 (1988).

Chu, et al., "Direct current reduces wound edema after full-thickness burn injury in rats", *J. Trauma*, 40(5):738-42 (1996).

Chu, et al., "Enhanced survival of autoepidermal-allodermal composite grafts in allosensitized animals by use of silver-nylon dressings and direct current", *J. Trauma*, 39(2):273-7; discussion 277-8 (1995).

Chu, et al., Weak direct current accelerates split-thickness graft healing on tangentially excised second-degree burns, *J. Burn Care Rehabil.*, 12(4):285-93 (1991).

Norm Din 54345 Teil 1, Prüfung von textilien elektrostatisches verhalten bestimmung eletrischer widerstandsgrössen (1992).

Barillo, et al. "Effect of silver-nylon dressings and weak direct current on skin microcirculation", Shock, 3:42 (suppl) (1995).

Chu, et al., Accelerated healing with a mesh autograft / allodermal composite skin graft treated with silver nylon dressings with and without direct current in rats\, J Trauma, 49 (1): 115-125 (2000).

Chu, et al., "Direct current reduces accumulation of Evans Blue albumin in full thickness burns", J Trauma., 47 (2): 294-299 (1999).

Fox, "Silver sulfadiazene—a new topical therapy for *Pseudomonas* in burns. Therapy of Pseudomonas infections in burns", Arch Surg., 96 (2):184-188 (1968).

Goetz, et al, "The oligodynamic effect of silver", Silver in Industry, edited by L. Addicks, Reinhold Publishing, New York, Chapter 16 401-29 (1940).

Grabb, et al., "Cutting the skin graft", Plastic Surgery, Third edition, Little, Brown and Co., Boston MA, p. 24 (1979).

Krizek and Robson, "Evolution of quantitative bacteriology in wound management", Am. J. of Surgery, 130:579-584 (1975).

Moyer, et al., "Treatment of large human burns with 0.5% silver nitrate solution" Arch Surg., 90:812-867 (1965).

Office Action in U.S. Appl. No. 10/421,370, mailed Jun. 13, 2011.

Office Action in U.S. Appl. No. 11/220,566, Office Action mailed Jul. 1, 2011.

Office Action in U.S. Appl. No. 11/745,237, Office Action mailed May 12, 2011.

Office Action in U.S. Appl. No. 11/929,804, Office Action mailed Apr. 26, 2011.

Office Action in U.S. Appl. No. 11/930,541, Office Action mailed Mar. 22, 2011.

Office Action in U.S. Appl. No. 90/011,455, Office Action mailed Jun. 23, 2011.

Shirani, et al. Silver-nylon dressings promote painless healing:, Proc. Am. Burn Assoc, 25:66 (1993).

Stanford and Fox, "Clinical experience with silver sulfadiazine, a new topical agent for control of pseudomonas infection in burn patients", J Trauma, 9 (5): 377-388 (1969).

US 5,872,068, 02/1999, Cartwright et al. (withdrawn)

* cited by examiner

FIG. 1
FIG. 2
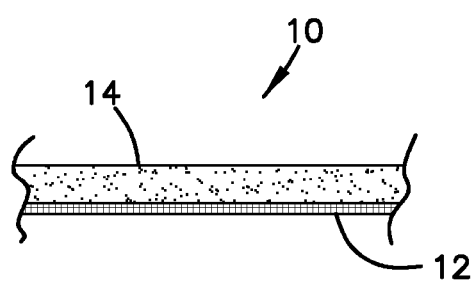
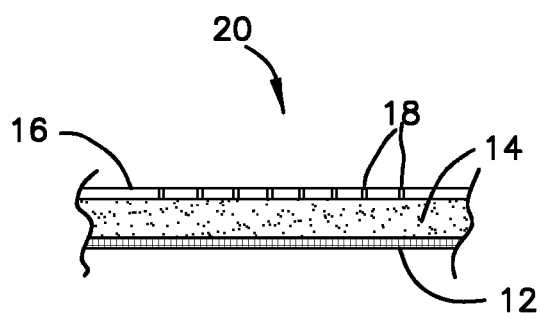
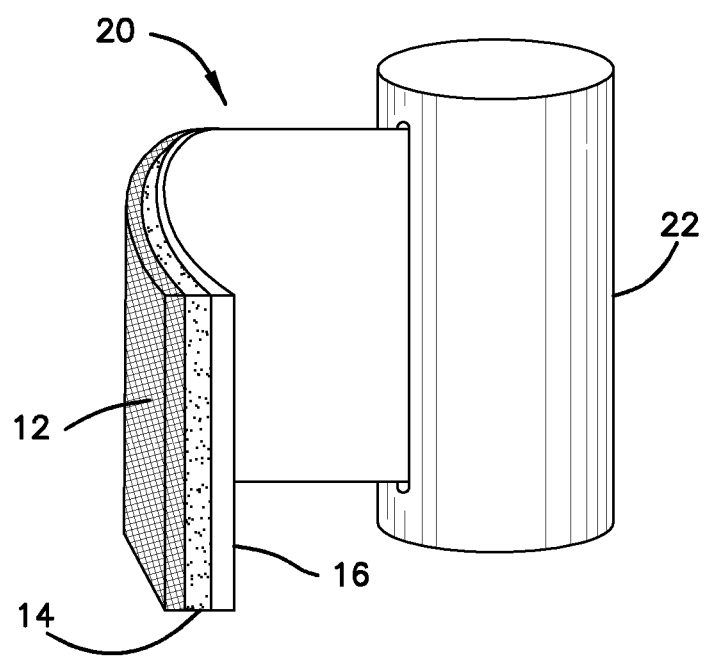
FIG. 3 ized on the surface of a plastic air splint or other bandaging
MULTILAYER LAMINATE WOUND DRESSING This application is a continuation of pending prior U.S. application Ser. No. 11/220,566 filed Sep. 6, 2005, which is a divisional of U.S. Ser. No. 08/707,779 filed Sep. 3, 1996, which is a continuation-in-part of application Ser. No. 08/524,134, filed Sep. 5, 1995 and 08/623,046 filed Mar. 28, 1996, now U.S. Pat. No. 5,814,094.

BACKGROUND OF THE INVENTION

1. Field of the Invention

The present invention relates to a multilayer dressing for the care and treatment of wounds. In particular, the present invention relates to a multilayer dressing having therapeutic and prophylactic properties, and methods for making the dressing.

2. Discussion of Background

The antimicrobial and antifungal properties of silver and silver compounds are well known. Topical preparations that contain silver or silver compounds—silver nitrate solution, silver sulfadiazine cream, colloidal silver compositions, silver-protein compounds such as Agyrol™, and so forth—are widely used in medicine. The useful effects of these compositions are due to the small amounts of free silver ions produced by dissociation of the silver compound or to formation of toxic by-products in situ.

The effectiveness of silver as an antimicrobial agent is at least partly determined by the delivery system. Most silver compounds that dissociate readily and produce large numbers of free silver ions are highly toxic to mammalian (including human) tissues. Less-toxic compounds, including silver sulfadiazine cream (widely used in the treatment of burns) and silver nitrate solution, do not dissociate readily and therefore do not release large numbers of silver ions. These compounds must re reapplied frequently to maintain their clinical efficacy.

Electrically-generated silver ions, which can penetrate more deeply into the tissues, are effective even against antibiotic-resistant strains of bacteria, fingi, etc., inhibiting growth in vivo and in vitro at current densities as low as 10 nA/mm$^2$ and silver ion concentrations as low as 0.5 mg/ml. The effects of electrically generated silver ions are described in a number of publications, including the following: J. A. Spadaro, et al., "Antibacterial Effects of Silver Electrodes with Weak Direct Current," *Antimicrobial Agents & Chemotherapy*, Vol. 6, pp. 637-642 (1974); T. J. Berger, et. al., "Antifungal Properties of Electrically Generated Metallic Ions," *Antimicrobial Agents & Chemotherapy*, Vol. 10, pp. 856-860 (1976); R. O. Becker, et al., Treatment of Orthopedic Infections With Electrically-Generated Silver Ions," *J. Bone & Joint Surgery*, Vol. 60-A, pp. 871-881 (1978)).

Silver and other metals are widely used in wound dressings and metals therefore. Fabo (U.S. Pat. No. 5,340,363) discloses a dressing that includes an outer absorbent layer and an inner porous, hydrophobic layer knitted of elastic threads and encapsulated by a soft, hydrophobic silicone or polyurethane gel. The gel can be used as a carrier for antibacterial agents such as zinc, pain-relieving substances, and agents that stimulate wound repair. Klippel, et al. (U.S. Pat. No. 3,830,908) use micronized allantoin as a carrier for a bactericidal or bacteristatic ingredient (such as silver citro allantoinate) that is dispersed on the surface of a plastic air splint or other bandaging product. McKnight, et al. (U.S. Pat. No. 3,800,792) disclose a surgical dressing having a layer of tanned, reconstituted collagen foam film laminated to a thin, continuous layer of an inert polymer. The collagen layer contains finely-divided silver metal added by soaking the collagen film in Tollen's reagent. Stowasser (U.S. Pat. No. 2,934,066) makes a dressing of absorbent, metal-coated fibers, such as a carding fleece coated with aluminum and backed by compressed cellulose, and polyamide fibers coated with vacuum deposited silver.

Dressings for provision of electric stimulation are also known. For example, Jones (U.S. Pat. No. 4,911,688) covers a wound with a clear cover that serves as a hallow chamber for holding a fluid such as saline in contact with a wound. When connected to a voltage source, a metal anode and a return electrode create free ions and electrical field to enhance healing and tissue regeneration. Juhasz (U.S. Pat. No. 4,817,594) discloses a multi-layer dressing for covering discharging, malodorous wounds. The dressing includes a layer of an electrically-conductive material such as silver and a layer of charcoal fabric. Application of a DC (direct current) voltage to a conductive layer drives silver ions into the wound to enhance tissue growth and inhibit bacterial growth; application of transcutaneous AC (alternating current) is used for post-operative pain relief. Seiderman (U.S. Pat. No. 4,767,401) describes a bandage-like device used for iontophoretic administration of medicaments, including silver-protein colloids. The device includes a metal foil electrode (preferably aluminum), and makes use of the slight inherent negative electric charge proximate a wound site to generate a small electric field at the site.

Matson (U.S. Pat. No. 4,728,323) coats a substrate (nylon fabric, polymeric film, fiberglass, gauze, or polyurethane foam) with a film of a silver salt deposited by vapor or sputter coating techniques. Alternatively, fibers can be coated and then woven or knitted into a fabric. Konikoff (U.S. Pat. No. 4,142,521) shows a bandage or surgical sponge material incorporating one or more electret elements, each electret providing a small electrostatic field to the area of the wound.

In application Ser. No. 08/524,134, filed Sep. 5, 1995, Becker, et al. disclose a bimetallic fabric woven of nylon fibers coated with a first metal such as silver, interspaced at intervals with fibers coated with a second metal such as gold or platinum, preferably in a ration of about 10:1. Alternatively, deposits of the second metal are placed on a fabric that contains the first metal. When contacted with an electrolyte, each contact junction between the first and second metals serves as a bimetallic junction that produces free silver ions. The material may be used in therapeutic or prophylactic treatment of wounds (including surgical incisions). An iontophoretic system for promoting tissue healing processes and inducing regeneration is described in application Ser. No. 08/623,046, filed Mar. 28, 1996. The system is implemented by placing a flexible, silver-containing anode in contact with the wound, placing a cathode on intact skin near the anode, and applying wound-specific DC voltage between the anode and the cathode. Electrically-generated silver ions from the anode penetrate into the adjacent tissues and undergo a sequence of reactions leading to formation of a silver-collagen complex. This complex acts as a biological inducer to cause the formation in vivo of an adequate blastema to support regeneration. The disclosures of the above-referenced patent applications are incorporated herein by reference.

Regardless of whether silver is provided in the form of silver ions or as a topical composition (silver nitrate solution, silver sulfadiazine cream, etc.), its beneficial effects are manifested primarily at the treated surface and immediate adjacent tissues, and are limited by the achievable tissue concentration of silver ions. Despite the availability of numerous techniques for the delivery of silver and silver compounds in vitro and in vivo, there remains a need for a delivery system that is capable of supplying clinically useful concentrations of silver ions to a treatment site without the need for adjuvant electrical stimulation.

SUMMARY OF THE INVENTION

According to its major aspects and broadly stated, the present invention is a flexible, multilayer dressing for therapeutic and prophylactic use, together with methods for making the dressing. The dressing includes a layer of fabric that contains a metal having bactericidal/bacteristatic properties, a layer of absorbent material, and, optionally, a layer of air-permeable and/or water-impermeable material. (For purposes of this description, a metal with "bactericidal properties" and/or "bacteristatic properties" is broadly defined as a metal that is active against at least one type of pathogenic agent, including bacteria, protozoa, fungi, rickettsiae, and viruses. Bactericidal agents kill organisms, whereas bacteristatic agents prevent their growth and multiplication.)

The multiplayer dressing is used in the care and treatment of skin infections and surface wounds (including surgical incisions), as a packing material for deep wounds, and as a swab for surface cleaning. In use, the dressing is effective in preventing the growth of pre-existing bacterial and fungal contaminants (particularly in traumatic wounds), and as a prophylactic measure against airborne contaminants (bacteria, fungi, etc.) and opportunistic infections.

A major feature of the present invention is the inner layer of the dressing, which contacts the wound surface when in use. The inner layer contains a bactericidal/bacteristatic metal preferably silver) loosely bound to a flexible, conformable fabric substrate. When the fabric is placed on the treatment site and contacted by saline, wound exudate, or water, at least a portion of the metal is released into the surrounding tissues with resulting beneficial effects. The inner layer may be made of metallized fibers of any suitable material, for example, it may be knitted or woven or silver-coated nylon fibers. Such a fabric is durable, nontoxic, nonhazardous, and inert until activated by contact with a suitable liquid.

An important feature of the present invention is the multilayer dressing itself. In a preferred embodiment of the invention, the dressing includes at least two layers: an inner layer of silver-containing fabric and a layer of moisture-absorbing material. Both layers are sufficiently flexible to conform to the area being treated, and can be provided in sizes and thicknesses suitable for the intended use. In this form, the dressing can be applied to surface wounds such as cuts (including surgical incisions), scrapes, and burns. It can also be applied to intact skin to treat localized infections, or used to pack deep wound cavities. For surface applications, the multilayer material may include a third, outer layer or an air-permeable and/or water impermeable material. If desired, a layer of a suitable adhesive can be added to adhere the dressing to the skin.

Another feature of the present invention is the method for making the dressing, which can be adapted for a variety of end uses. The dressing may be made by any convenient techniques known in the art, of readily available, generally inexpensive materials. It may be provided in a convenient form for a variety of applications, ranging from individual BAND-AID®-type dressings to rolls or sheets that can be cut to any needed size. For example, a two-layer dressing approximately 4" wide and 3', long (about 10×90 cm), wherein the absorbent layer is no more than 2-3 times as thick as the silver fabric layer, is useful for packing deep wound cavities. On the other hand, a three-layer dressing with an air-permeable outer layer may be preferred for a burn or surgical incision.

Other features and advantages of the present invention will be apparent to those skilled in the art from a careful reading of the Detailed Description of a Preferred Embodiment presented below and accompanied by the drawings.

BRIEF DESCRIPTION OF THE DRAWINGS

In the drawings,

FIG. 1 is a cross-sectional view of a multilayer dressing according to a preferred embodiment of the present invention;

FIG. 2 is a cross-sectional view of a multilayer dressing according to another preferred embodiment of the invention;

FIG. 3 is a perspective view of the multilayer dressing of FIG. 2, shown packed in a dispenser;

DETAILED DESCRIPTION OF THE PREFERRED EMBODIMENT

Figure 4:
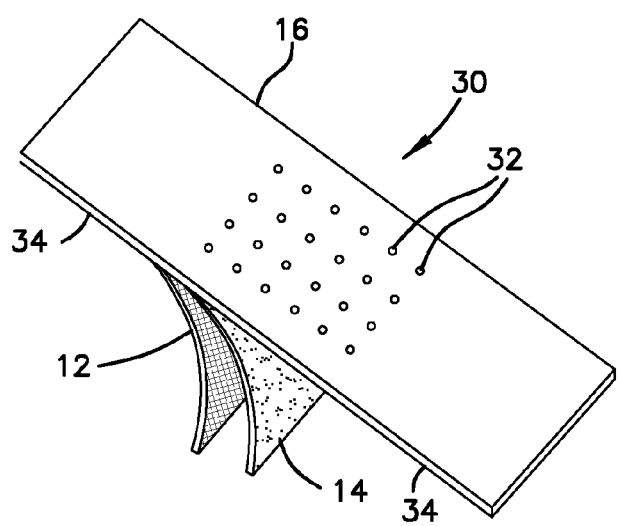
FIG. 4 is a perspective view of another multilayer dressing according to the invention.

In the following detailed description, reference numerals are used to identify structural elements, portions of elements, surfaces and areas in the drawings. For consistency, whenever the same numeral is used in different drawings, it indicates the same element, portion, surface and area as when first used.

Referring now to FIG. 1, there is shown a cross-sectional view of a multilayer material 10 according to a preferred embodiment of the present invention. Multilayer material 10 includes a first layer 12 of a silver-containing fabric and a second layer 14 of a moisture-absorbent material.

First layer 12 consists of a flexible, conformable metallized fabric made by weaving, knitting, crocheting, felting, blowing, or some other convenient process. Preferably, first layer 12 is made of silver-coated nylon fibers. However, other materials may also be suitable, including nonwoven sheet material that incorporate or are coated with suitable amounts of silver.

Silver (or some other metal with medically useful bactericidal/bacteristatic properties) may be added to the fibers of layer 12 by vapor coating, aerosolized deposition, sputter coating or other standard techniques known in the art. Individual fibers can be coated and then worked (woven, knitted, crocheted, felted, blown, etc.) into fabric. Alternatively, suitable amounts of silver may be added to the finished fabric. While the thickness of such a silver coating may vary broadly, the amount of silver should be such that layer 12 has a specific resistance no greater than approximately 5 $\Omega$/cm; most preferably, layer 12 has a specific resistance no greater than approximately 1 $\Omega$/cm. Typically, a medically-useful material for layer 12 contains at least approximately 5 wt. % silver, preferably approximately 20 wt. % silver. However, the metal content and specific resistance of layer 12, as well as the thickness and uniformity of the coating, may vary broadly depending on the selected metal and the intended uses of dressing 10. Thus, fabrics with lesser amounts of metal may also be useful in the practice of the invention. Materials with higher resistance (and lower silver content) may also be useful; however, such materials will generally be incapable of supplying the needed amounts of free silver to the treatment site.

Layer 12 should also not only be made of a material having a sufficiently high content of silver (or other suitable metal), but the silver should be approximately uniformly distributed.

Non-uniform distribution means that the wound will not be uniformly treated: the amount of silver supplied to different areas will differ.

The silver in layer 12 is releasably attached to the fabric substrate so that, when layer 12 is placed in contact with body tissues and moistened by a suitable liquid, at least a portion of the silver migrates into the adjacent tissues. While not wishing to be bound by theory, it is believed that metallized fabrics wherein the metal atoms are somewhat loosely bound to the molecules of the fabric substrate (forming a chemical or physical complex with the substrate rather than being simply deposited onto it) are especially suitable for the practice of the present invention. In a complex of this nature, the bond energy is sufficiently low to permit effusion of the metal when the fabric is wet.

Second layer 14 is made of a soft, flexible, moisture-absorbent material capable of seeping up wound exudates, such as woven or nonwoven cotton (layer 14 may be moistened with water, normal saline, or other suitable liquid when dressing 10 is in use). Layer 14 need be no more than approximately 0.1-0.5 cm thick; however thicker layers may be useful when material 10 is used in the care of draining wounds.

Multilayer material 10 is inert until moistened by water, wound exudate, normal saline, or other liquid. Then, the bonds between the silver atoms and the fabric substrate of first layer 12 are loosened and at least some of the silver migrates from the fabric into the surrounding tissues. When placed on a wound with first layer 12 contacting the body surface, naturally-occurring body fluids may be sufficient to activate material 10. However, a suitable liquid (normal saline, Ringer's solution, tap water and the like) must generally be applied to ensure release of silver from layer 12.

Another multilayer material according to the present invention is shown in FIG. 2. A material 20, like above-described material 10, includes a metal-containing layer 12 and a moisture-absorbing layer 14. Adjacent to layer 14 is a thin, flexible outer layer 16 made of nonporous plastic material, with a plurality of perforations 18 therethrough. Outer layer 16 may be made of an air-permeable, moisture-impermeable material such as GORETEX®. Alternatively, layer 16 may be a plastic material such as the materials used in commercially-available dressings (BAND-AID®, CURAD®, etc.)

Materials 10 and 20 may be finished in dimensions to suit various applications, for example, 2" (about 5 cm) widths for covering surgical incisions and relatively small wounds, and 12" (about 30 cm) or larger widths for covering large wounds such as burns, and cut to any needed length. When made in sections approximately 4"×3' (about 10×90 cm) and with an absorbent layer 14 no thicker than approximately 2-3 times the thickness of layer 12, material 10 is useful as a packing material for deep wounds. Material 20 (or material 10) may be packed in a dispenser 22 for shipping, storage, and eventual use (FIG. 3).

Materials 10 and 20 may be used in a variety of wound dressings to provide prophylactic and/or therapeutic activity to help prevent (or treat) infection and facilitate healing. The dimensions and configuration of such dressings depend on the size and location of the area to be treated, and requires a means for affixing the dressing in place, controlling moisture loss from the wound, and ensuring direct contact between the layer 12 and the actual wound surface itself.

A wound dressing 30 according to the present invention is shown in FIG. 4. Dressing 30 includes a thin, flexible outer layer 16, an absorbent layer 14 attached to the medial portion of layer 16, and at least one inner layer 12 of silver-containing fabric (layers 12 and 14 are shown pulled away from layer 16 for clarity). Perforations (18) in the medical portion of layer 16 provide added ventilation of the wound surface to assist in epitheliazation. An inner side 34 of layer 16, on either side of layers 12, 14, may be coated with adhesive and protected with a removable strip of material (not shown) that is peeled off just prior to use. Dressing 30 is flexible and, via the adhesive coating on layer 32, capable of adhering to dry skin. In use, wound exudate (or some other liquid) moistens layer 12 and passes therethrough to absorbent, moisture-retaining layer 14.

Figure 5:
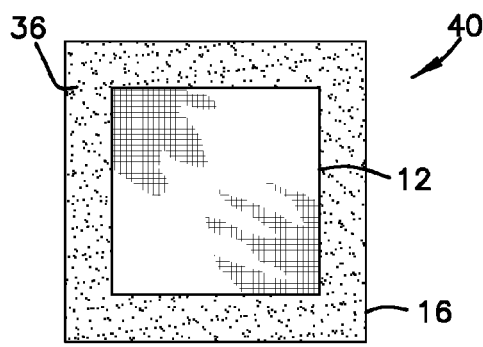
FIGS. 5-7 are plan views of additional multilayer dressings according to the invention.
Figure 6:
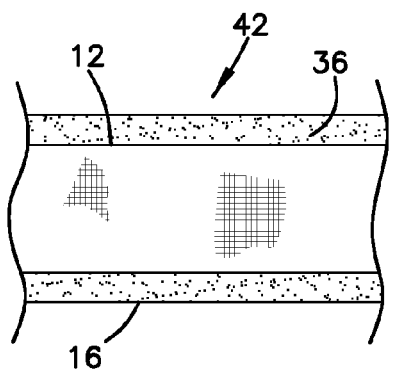

Another wound dressing 40 is shown in FIG. 5. Dressing 40 is made of material 20, thus, includes a silver-containing layer 12, an absorbent layer 14 (not shown), and an outer layer 16 having a larger area than layer 12. A layer of adhesive 36 coats the inner side of layer 16, generally as shown. A dressing 42 with adhesive margins 36 may be furnished in a strip of any convenient length (FIG. 6). Adhesive 36 may be covered by a peel-off strip (not shown) prior to use. Dressings 40, 42 may, of course, be made in any convenient sizes.

Figure 7:
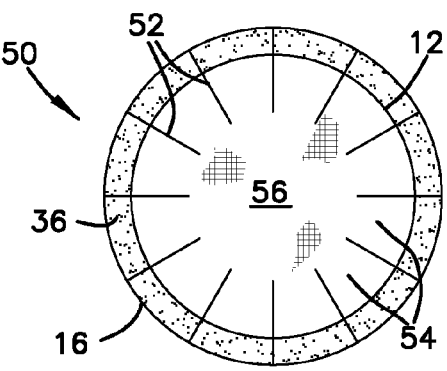

A wound dressing 50 adapted for placement on fingertip wounds is shown in FIG. 7. Dressing 50, like dressing 40, is made of material 20 and has an outer layer 16 that is larger in area than silver-containing layer 12 and a layer of adhesive 36 coating the inner side of layer 16. A plurality of radial slits 52 extend inwards from the periphery of dressing 50, to form a series of flaps 54 about a central portion 56. Dressing 50 preferably has at least four slits 52 forming four flaps 54. However, a greater number of slits 52, such as the twelve slits 52 at approximately 30° intervals shown in FIG. 7, are preferred.

In use, portion 56 is centered on the fingertip with layer 12 adjacent to the skin. Flaps 54 are affixed to the skin by adhesive 36, distal to wound. By overlapping flaps 54, the user can form dressing 50 into a "cap" that covers the fingertip. While human digits vary widely in size, a dressing 50 approximately 2" (about 5 cm) in diameter with a central portion 56 approximately 1" (about 2.5 cm) in diameter is suitable for most. However, dressing 50 can easily be made in different sizes to better fit very small or very large digits.

Multilayer materials 10, 20 (and dressings made with the materials) are flexible, easily re-shapeable and conformable to the region to be treated. Materials 10, 20 can be used for treating surface wounds such as cuts, scrapes, and burns, and also be used for filling in deep wound cavities, thereby enabling the wound edges to be kept apart during the healing process.

In use, materials 10, 20 (or dressings such as dressings 30, 40, 42, 50) are applied to the skin after appropriate surface preparation (dressings 30, 40, 42 are preferably applied to dry skin so that adhesive 36 adheres well to the skin to hold the dressing in place). Depending on the area to be treated, the layers 12, 14 may be moistened to stimulate release of silver from the material. Silver is released from layer 12 and migrates into the area to minimize external and cross-contamination of the treatment site, and help prevent bacterial and fungal infections, while not hindering normal cell growth or repair. No toxic substance is introduced into the patient's body. Materials 10, 20 (and dressings that contain these materials) are preferably replaced daily; however, the materials can be safely left in place for as long as 3 days if circumstances so require. The materials can be used for prophylactic treatment of fresh wounds and surgical incisions, treatment or prevention of early stage decubital ulcers ("bed sores"), therapeutic treatment of infected and traumatic wounds, and so forth.

The present invention is further illustrated in the following nonlimiting examples.

EXAMPLE 1

The effectiveness of warp knit silver nylon fabric (specific resistance about 1 Ω/cm) in inhibiting the growth of three common strains of bacteria (*S. aureus, E. coli* and *P. aeuginosa*) was tested in vitro. The bacterial cultures were planted in agar-filled petri dishes using the Kirby Bauer technique, one culture per dish. Sterilized 1-cm squares of the fabric were placed on the surfaces of the cultures. Every twenty-four hours, each fabric square was removed from the culture medium and replanted in a different area of the same dish. After 72 hours, the culture medium directly underneath the fabric squares was clear (i.e., the bacteria in those regions had been killed). In addition, all areas where the fabric squares had been placed previously remained clear.

EXAMPLE 2

The warp knit silver nylon fabric of Example 1 was found to cause dedifferentiation of mammalian cell in vitro. The observed effects were proportional to the concentration of silver ions in the culture medium and inversely proportional to distance from the fabric: the closer to the fabric, the greater the concentration of dedifferentiated cells and the greater the silver ion concentration.

EXAMPLE 3

The effectiveness of silver sulfadiazine cream, silver nylon fabric, and plain nylon fabric in inhibiting the bacterial growth was compared (L. Smee, "The Effectiveness of Silver Nylon Cloth and Silver Sulfadiazine Cream as Antiseptics," Piedmont College Senior Thesis, April, 1996). Five common strains of bacteria were studied including two gram-negative strains (*E. coli, P. aeruginosa*) and three gram-positive strains (*E. faecalis, S. aureus, S. pyogenes*).

Each strain of bacterium was inoculated into three agar-filled petri dishes. Following the inoculation, three fabric disks were placed into each dish: a disk of plain nylon cloth which served as a control, a disk of silver nylon fabric, and a plain nylon disk which has been coated with silver sulfadiazine cream. Each disk had a surface area of 3.4 mm². The dishes were incubated for seventy-two hours, and removed every twenty-four hours to measure the inhibition zone around each disk (i.e., the distance from the outer edge of the fabric disk to the perimeter of the clear zone of the inhibited bacterial growth about the disk).

Results indicated that the silver nylon fabric and silver sulfadiazine cream were effective bacterial grown inhibitors against all tested strains. Average results for two trials are listed in Table I.

TABLE I

Inhibition zones (mm) for silver nylon fabric (Ag Nylon), nylon fabric with silver sulfadiazine cream (Nylon + Ag Cream), and plain nylon fabric (Nylon). Results shown represent the average of two trials.

| | Ag Nylon | Nylon + Ag Cream | Nylon |
|---|---|---|---|
| *E. coli* | | | |
| Day 1 | 7.4 | 6.3 | -0- |
| Day 2 | 9.2 | 6.4 | -0- |
| Day 3 | 10 | 7.2 | -0- |
| *P. aeruginosa* | | | |
| Day 1 | 57 | 32 | -0- |
| Day 2 | 59 | 29 | -0- |
| Day 3 | 62 | 29 | -0- |
| *E. faecalis* | | | |
| Day 1 | 8.9 | 4.0 | -0- |
| Day 2 | 11 | 3.8 | -0- |
| Day 3 | 15 | 2.4 | -0- |
| *S. aureus* | | | |
| Day 1 | 9.3 | 7.1 | -0- |
| Day 2 | 9.5 | 2.1 | -0- |
| Day 3 | 12 | 0.9 | -0- |
| *S. pyogenes* | | | |
| Day 1 | 57 | 28 | -0- |
| Day 2 | 66 | 34 | -0- |
| Day 3 | 70 | 38 | -0- |

These results indicate that silver nylon fabric is an effective antimicrobial agents. In Example 3, the fabric proved to be more effective than silver sulfadiazine cream, creating and maintaining a larger inhibition zone for each strain tested for the duration of the experiments.

As a delivery system for silver, a fabric with a sufficiently high concentration of silver releases silver ions at a steady rate for as long as the fabric is in contact with the culture medium (in vitro or in vivo). Such a fabric does not cause allergic reactions, thus, its use prevents other potentially-harmful side effects associated with other delivery systems (silver sulfadiazine, silver thiosulfate). A multilayer dressing using the fabric is nonhazardous, conformable to the shape of the site to be treated, readily adaptable to diverse clinical situations, and safe and easy to use. When treating patients with extensive burns, a dressing according to the invention is less expensive, less cumbersome, and more effective than silver sulfadiazine cream.

It will be apparent to those skilled in the art that many changes and substitutions can be made to the preferred embodiment herein described without departing from the spirit and scope of the present invention as defined by the appended claims.

What is claimed is:

1. A wound dressing, comprising:
a flexible, conformable fabric substrate comprising an effective amount of silver-coated fibers worked into or forming the flexible, conformable fabric substrate to passively release an effective amount of silver from the wound dressing into a wound at a steady rate for as long as three days when the wound dressing contacts saline, wound exudate or water at the wound, wherein the flexible, conformable fabric substrate has a specific resistance no greater than approximately 5 μ/cm.

2. The wound dressing of claim 1, wherein the flexible, conformable fabric substrate comprises at least approximately 5 wt. % silver.

3. The wound dressing of claim 1, wherein the flexible, conformable fabric substrate comprises at least approximately 20 wt. % silver.

4. The wound dressing of claim 1, wherein the flexible, conformable fabric substrate has a specific resistance no greater than approximately 1 Ω/cm.

5. The wound dressing of claim 1, wherein the silver is loosely bound to the plurality of fibers.

6. The wound dressing of claim 1, wherein the wound is a traumatic wound.

7. The wound dressing of claim 6, wherein the traumatic wound is a decubital ulcer.

8. A wound dressing, comprising:
a flexible fabric substrate comprising silver-coated fibers; and
a layer of moisture-absorbing material attached to said substrate, wherein the silver and the substrate have a combined weight, wherein the quantity of silver is at least approximately 5 wt. % of the combined weight, and wherein an effective amount of silver is passively released at a steady rate for as long as three days at a treatment site from the wound dressing without application of an electric current when the wound dressing contacts saline, wound exudate or water at the treatment site.

9. The wound dressing of claim 8, wherein the silver and the substrate have a combined weight, and wherein the silver is at least approximately 20 wt. % of said combined weight.

10. The wound dressing of claim 8, wherein the fibers are nylon.

11. The wound dressing of claim 8, further comprising a third layer adjacent to said layer of moisture-absorbing material, said third layer made of water-impermeable material.

12. The wound dressing of claim 8, further comprising a third layer adjacent to said layer of moisture-absorbing material, said third layer made of an air-permeable material.

13. The wound dressing of claim 8, wherein said moisture-absorbing material is made of cotton.

14. The wound dressing of claim 8, further comprising an adhesive layer attached to at least a portion of said moisture-absorbing material said for adhering said dressing to intact skin.

15. The dressing as recited in claim 8, further comprising:
a third layer adjacent to said layer of moisture-absorbing material, said third layer made of a water-impermeable material; and
an adhesive carried by at least a portion of said third layer, said adhesive positioned so that said adhesive adheres to intact skin when said dressing is placed in contact with a wound.

16. The wound dressing of claim 8, wherein the moisture-absorbing material absorbs wound exudate through the fabric substrate.

* * * * *

UNITED STATES PATENT AND TRADEMARK OFFICE
CERTIFICATE OF CORRECTION

PATENT NO. : 8,293,964 B2
APPLICATION NO. : 11/927065
DATED : October 23, 2012
INVENTOR(S) : Robert O. Becker et al.

It is certified that error appears in the above-identified patent and that said Letters Patent is hereby corrected as shown below:

In the Claims:

Claim 1, column 8, line 61, replace "µ/cm" with --Ω/cm--.

Signed and Sealed this
Thirtieth Day of April, 2013

Teresa Stanek Rea
*Acting Director of the United States Patent and Trademark Office*